United States Patent [19]
Bombardelli et al.

[11] Patent Number: 5,795,575
[45] Date of Patent: Aug. 18, 1998

[54] TOPICAL MEDICAMENT WHICH INCREASES THE NUMBER OF CAPILLARIES IN DAMAGED SKIN

[75] Inventors: Ezio Bombardelli; Sergio Curri; Giancarlo Guglielmini; Paolo Morazzoni; Walter Polinelli, all of Milan, Italy

[73] Assignee: Indena S.p.A., Milan, Italy

[21] Appl. No.: 763,925

[22] Filed: Dec. 12, 1996

Related U.S. Application Data

[63] Continuation of Ser. No. 434,091, May 3, 1995, abandoned.

[30] Foreign Application Priority Data

May 6, 1994 [IT] Italy .................. MI94A0884

[51] Int. Cl.⁶ .................................. A61K 39/385
[52] U.S. Cl. ..................... 424/195.1; 424/283.1; 424/78.6; 424/78.02; 514/886; 514/887
[58] Field of Search .................. 424/195.1, 283.1, 424/78.06, 78.02; 514/886, 887

[56] References Cited

U.S. PATENT DOCUMENTS

| | | | |
|---|---|---|---|
| 3,903,882 | 9/1975 | August | 128/155 |
| 4,489,066 | 12/1984 | Fedeli | 424/181 |
| 4,719,111 | 1/1988 | Wilson | 424/195.1 |
| 5,093,354 | 3/1992 | Viehmann et al. | 514/428 |
| 5,104,655 | 4/1992 | Bombardelli et al. | 424/195.1 |
| 5,176,919 | 1/1993 | Curri et al. | 424/450 |
| 5,280,020 | 1/1994 | Curri | 514/78 |
| 5,334,385 | 8/1994 | Bombardelli | 424/195.1 |
| 5,403,867 | 4/1995 | Okumura et al. | 514/573 |
| 5,484,833 | 1/1996 | Bombardelli | 424/449 |

FOREIGN PATENT DOCUMENTS

| | | |
|---|---|---|
| 0 304 603 | 3/1989 | European Pat. Off. |
| 0 369 105 | 5/1990 | European Pat. Off. |
| 0 418 806 | 3/1991 | European Pat. Off. |
| 0 442 063 | 8/1991 | European Pat. Off. |
| 0360556 | 4/1993 | European Pat. Off. |
| 0 573 260 | 12/1993 | European Pat. Off. |
| 0161388 | 12/1981 | Japan. |

*Primary Examiner*—David M. Naff
*Assistant Examiner*—Deborah Ware
*Attorney, Agent, or Firm*—Pennie & Edmonds LLP

[57] ABSTRACT

A method for increasing the number of capillaries in damaged skin during healing of the skin is disclosed. The method includes the application of a skin composition to the damaged skin which comprises an active compound having peripheral vasokinetic activity and a pharmaceutically acceptable carrier. The active compound is selected from compounds such as *Amni visnaga* coumarins, Vinca alkaloids, Ergot alkaloids, polyunsaturated fatty acid derivatives, a buflomedil bioflavinoid, Ginkgo bioflavonoids, and Cratageus bioflavonoids. The composition is applied in amount to increase the number of capillaries in new tissue which forms during healing of the damaged skin. Furthermore, a method of treating bedsores is also disclosed.

23 Claims, No Drawings

TOPICAL MEDICAMENT WHICH INCREASES THE NUMBER OF CAPILLARIES IN DAMAGED SKIN

This is a continuation of application Ser. No. 08/434,091, filed May 3, 1995, now abandoned.

FILED OF THE INVENTION

The present invention relates to topical medicaments having cicatrizing activity, particularly to the use of compounds having vasokinetic activity for the manufacture of topical medicaments useful for the treatment of wounds and scars.

BACKGROUND OF THE INVENTION

The wound healing process comprises the quick regeneration of the damaged tissues. Such a phenomenon involves a quick, disordered cell proliferation in order to restore as soon as possible the integrity of the damaged part. The process of wound healing ends with cicatrization, i.e. the formation of fibrous connective tissue which restores the damaged part of the epidermis. Due to the quick, disordered growth of cicatricial tissue, usually the formation of keloids of unpleasant appearance occurs. This problem is particularly felt in plastic surgery, wherein the operations, however accurate, often leave scars in body parts that may usually be seen.

The cicatrizing medicaments known today exert their action through the stimulation of the reparative process or they only maintain an environment favourable to this process, for example topical medicaments containing collagen, or antibiotic combinations respectively.

As far as the Applicant knows, up to now the problem of modulating the cicatrization process in order to reach a uniform healing of the wound, without unaesthetic keloids, has not been solved.

Compounds having vasokinetic activity have been known for some time for the treatment of circulation disorders, in particular of peripheral circulation.

Italian Patent n. 1,223,290, in the Applicant's name, discloses the use of polyunsaturated fatty acid derivatives for the treatment of functional or organic peripheral vasculopathies, such as Raynaud's disease, alopecia, impotentia erigendi, and for aesthetic applications.

Italian Patent n. 1,233,753, in the Applicant's name, discloses the micro-vasculokinetic and hypersphygmicizing activities of extractive or semi-synthetic derivatives of *Amni visnaga* and *Amni majus*.

Other substances known for their vasokinetic activity which are comprised in the present invention are the Vinca alkaloids, such as raubasine, tetrahydroalstonine and derivatives thereof, vincamine and derivatives, eburnamonine and derivatives; the Ergot alkaloids and derivatives thereof; bioflavonoids such as those obtained from Ginkgo biloba, prepared according to EP 0 360 556 B1, Cratageus sp., buflomedil.

SUMMARY OF THE INVENTION

Now it has surprisingly been found that compounds having vasculokinetic activity, when applied topically on wounds of surgical origin after suturing or on already healed scars, lead to a remarkable improvement in the healing time while also improving the quality of the scar. Such compounds also prevent and cure bedsores. Thus the present invention relates to methods of using such compounds for the treatment of wounds and for the prevention of bedsores.

It is believed that substances generally having vasokinetic activity are useful for the purposes of the present invention.

An object of the present invention is the use of substances having vasculokinetic activity for the manufacture of a topical medicament useful for the treatment of wounds and scars.

The compounds having vasokinetic activity can be used as such or in the form of natural or semi-synthetic derivatives.

A further object of the present invention is the use of extracts containing substances having vasokinetic activity for the preparation of a topical medicament useful for the treatment of wounds and scars.

DETAILED DESCRIPTION OF THE INVENTION

In a first preferred embodiment, the present invention provides the use of *Amni visnaga* derivatives, in particular of the coumarins khellin and visnadine more preferably khellin.

In another embodiment, the present invention provides for the use of Vinca alkaloids, such as vincamine and raubasine, Ergot alkaloids, ethyl xhimeninate and buflomedil.

In order to evaluate the activity of the compounds having vasokinetic activity, a clinical study was carried out on patients and healthy volunteers.

O/W Formulations containing khellin in percentages of 0.25, 0.5 and 1% by weight were prepared. For the acute evaluations the 1% formulation was used, whereas for long term treatment the 0.5% formulation was employed.

A group of healthy volunteers (26 subjects, 7 males, 19 females, age 22–45 ; mean age 33±11.2), admitted according to the criterion of clinical integrity of the arm skin and the non-intake of corticosteroids or other antiinflammatory drugs during the last 5 days preceding the test, were treated with occlusive pads of 4 $cm^2$ size imbued with the 0.5% formulation, applied on the skin and kept for 3 days.

At the end of the 3rd day the pad was removed and after 7 days the treatment was repeated under the same conditions. At the end of the treatment, the skin was examined for the presence of reddening, using evaluation scores from 1 to 4 versus placebo (olive oil).

In this evaluation, 0 means no reaction, 4 very intense reaction with reddening associated with dryness and desquamation of the skin and a burning sensation during the subsequent day.

Compounds proved to be perfectly tolerated.

A group of 6 patients who had undergone plastic surgery (removal of naevi, etc.) were treated with 1 g of the 1% formulation applied on the suturated wound by means of a gentle massage. The patients were examined for the neoformation of capillaries during the healing process of the surgical wound. The study was carried out by capillaroscopy, in the following named OPCV (Optical Probe Video Capillaroscopy). The instrumentation used was a Moritex Optical Probe Capillaroscope Scopemann 504 (Alfa Strumenti, Milan, Italy) equipped with contact lenses 50×, 200× and 400×. Two original methods were used to evaluate quantitatively the capillary density. In the first method, the OPVC working station was connected with the Capi-Flow System according to Bollinger and Fogrell. In the second method, the OPVC working station was connected with a RISC image-analyzer, using software for digitalizing the image Archimedes of Cambridge.

An analysis with a Laser Doppler Flowmeter (Periflow 2b, Perimed, Sweden) was also performed.

The topical administration of khellin is followed by a marked increase in the number of capillaries. The rates of the flow and of the blood volume are substantially enhanced, whereby capillaries formerly empty become full with blood. These phenomena can be observed in a time ranging from 15 to 45 minutes after the application.

For the evaluation of the actual effect of the above mentioned substances, patients who had undergone surgery, for example having wounds larger than 2 cm, were treated after suturation for one centimetre with a placebo formulation and for one centimetre with a formulation containing a vasoactive molecule.

The effect on the wounds appeared as a marked increase in the number of capillaries, together with an increase in the high frequency rhythmic variations, as measured with the Doppler. The most important result was the observation that the neo-formed capillaries were arranged parallel to the skin surface, in the form of long continuous rows, which traverse the whole length of the scar and the discontinuous capillary network of the zone contra-lateral to the scar.

Similar results were obtained with topical medicaments according to the present invention containing as active ingredient other compounds such as visnadine, vincamine, raubasine, nicergoline, ethyl xhimeninate, buflomedil, bioflavonoids obtained from Ginkgo biloba and Cratageus sp.

The results reported above prove that the medicaments according to the present invention are capable of inducing an active hyperemia in the cicatricial area, useful in the modulation of the cicatrization itself, with the double effect of decreasing the healing time and that of elimination of the unaesthetism accompanying the reparative process.

Along with such a reparative process, it has surprisingly been found, and it is one of the objects of the invention, that the products themselves, or the formulations containing them, when administered topically on ulcers and varices due to venous insufficiency lead to a rapid, orderly cicatrization process. Particularly, the formulations containing these products in a silicone carrier proved specifically useful in the prophylactic and therapeutical treatment of decubitus sores.

It has surprisingly been found that applying on one of the contra-lateral sacral parts of bedridden persons, the products of the invention and on the other part a placebo formulation, under otherwise identical conditions, no sores formed on the treated area, contrarily to the other one.

In subjects with amputated limbs who could not tolerate prostheses, it has surprisingly been found that the administration of khellin or Visnadine leads to the resolution of the problem improving the cicatricial angiotettonic after a two-week treatment with formulations containing 3% of one of the two products.

The Applicant believes that the microvasculokinetic activity of the topical medicaments object of the present invention plays a paramount role in the fast removal of the degradation catabolites of necrotic tissue, moreover leading to an oriented capillarogenesis; however, the invention is not intended to be limited by any theoretical consideration.

The topical medicaments for the treatment of wounds and scars according to the present invention are prepared according to conventional methods known to those skilled in the art, for example as described in "Remington's Pharmaceutical Sciences Handbook" XVII ed. Mack Pub. Inc.; New York, U.S.A.". According to the present invention, the topical medicaments can be in the form of salves, ointments, creams, lotions, solutions, suspensions, sticks, sprays, plasters and medicated bandages. In particular, the topical medicaments can be in the form of formulations with a high saturated and unsaturated phospholipid content. The topical medicaments according to the present invention can also be combined with other known medicaments with cicatrizing activity, chemotherapeutic, antimicrobial, immune stimulating agents, collagen, hyaluronic acid, and the like.

The topical medicaments according to the present invention contain one or more compounds with vasokinetic activity in an amount from 0.01 to 10% by weight.

The single doses of the posology will be determined by the physician, anyway by way of example the applications may be one or more daily for a time from one day to about one month, depending on the requirements.

The following examples further illustrate the invention.

EXAMPLE I

Preparation of a cream containing khellin
    3% khellin cream
    100 g of cream contain:
        Khellin 3.00 g
        Isopropyl Myristate 10.00 g
        Phosphatidyl choline (Phospholipon 90-Nattermann) 5.00 g
        Cetyl alcohol 6.00 g
        Tween 60 3.00 g
        Silicone oil 350 (Tegiloxan 350-Tego) 0.50 g
        α-Tocopherol 0.20 g
        Ascorbyl palmitate 0.10 g
        Propylene glycol 4.00 g
        Methyl p-OH benzoate 0.20 g
        Disodium edetate 0.10 g
        Imidazolidinylurea (Gram 1) 0.30 g
        Carbopol 5-984 0.40 g
        10% sodium hydroxide sol. 1.00 g
        Distilled water q.s. to 100.00 g

EXAMPLE IIa

Preparation of a gel containing Ginkgo biloba dimeric flavons
    0.5% Gel containing Ginkgo Biloba dimeric flavons
    100 g gel contain:
        Ginkgo Biloba Dimeric flavons 0.50 g
        Preservatives q.s.
        Hydroxyethyl cellulose 2.00 g
        (Natrosol 250-aqualon) Distilled water q.s. to 100.00 g

EXAMPLE IIb

Preparation of a gel containing Ginkgo Biloba dimeric flavons
    3% Gel containing Ginkgo Biloba dimeric flavons
    100 g contain:
        Ginkgo Biloba dimeric flavons 3.00 g
        Glyceryl Stearate and Peg-100 stearate (Glicmonos A2000-Comiel) 8.00 g
        Cetyl alcohol 3.00 g
        Polyisoprene (Syntesqual Vevy) 4.00 g
        Wheat germ oil 4.00 g
        Dimethicone 350 cps 0.50 g
        α-Tocopherol (Vitamin E-Fluka) 0.20 g
        Ascorbyl palmitate 0.10 g
        Imidazolidinylurea (Gram 1) 0.30 g
        Carbomer 934 (Carbopol 934P-Goodrich) 0.50 g
        Polysorbate 80 (Tween 80-ICI) 2.00 g
        10% sodium hydroxide sol. 1.00 g
        Perfume 0.20 g
        Distilled water q.s. to 100.00 g
        pH 6.2

EXAMPLE III
Preparation of an ointment containing visnadine
1.5% Visnadine ointment
100 g of ointment contain:
  Visnadine 1.50 g
  Isopropyl Myristate 5.00 g
  Phosphatidyl choline (lipoid s100-Lipoid) 3.00 g
  Cetyl alcohol 5.00 g
  Tween 60 3.00 g
  Silicone oil 350 (Tegiloxan 350-Tego) 0.50 g
  Propylene glycol 5.00 g
  Disodium edetate 0.10 g
  Carbopol 5-984 0.40 g
  10% sodium hydroxide sol. 1.80 g
  Perfume q.s.
  Antioxidant q.s.
  Preservatives q.s.
  Distilled water q.s. to 100.00 g

EXAMPLE IV
Preparation of a gel containing buflomedil
0.5% Buflomedil Gel
100 g contain:
  Buflomedil 0.50 g
  Preservatives q.s.
  Hydroxyethyl cellulose 2.00 g
  (Natrosol 250-aqualon)
  Distilled water q.s. a 100.00 g

EXAMPLE V
Preparation of an ointment containing vincamine
1% Vincamine ointment
100 g contain:
  Vincamine 1.00 g
  Carbomer 934 (Carbopol 934-Goodrich) 0.50 g
  Imidazolidinylurea 0.30 g
  Kathon CG 0.05 g
  Disodium edetate 0.10 g
  Glyceryl stearate the Peg-100 stearate (Glicmonos A2000-Comiel) 0.50 g
  Cetyl Palmitate (Cutina CP-Henkel) 2.00 g
  Polyisoprene (Syntesqual-Vevy) 5.00 g
  Modified jojoba oil (Cetiol J600-Henkel) 5.00 g
  Dimethicone 350 (Tegiloxan-Tego) 0.50 g
  Tocopherol 0.20 g
  Ascorbyl palmitate 0.10 g
  10% sodium hydroxide sol. 0.80 g
  Perfume 0.10 g
  Distilled water q.s. to 100.00 g.

We claim:

1. A method for increasing the number of capillaries in damaged skin during healing thereof which comprises applying to damaged skin a composition comprising an active compound having peripheral vasokinetic activity and a pharmaceutically acceptable carrier, wherein said active compound is selected from the group consisting of *Amni visnaga* coumarins, Vinca alkaloids, Ergot alkaloids, polyunsaturated fatty acid derivatives, a buflomedil bioflavinoid, Ginkgo bioflavonoids, and Cratageus bioflavonoids, and is applied in an amount effective to increase the number of capillaries in new tissue which forms during healing of the damaged skin.

2. The method of claim 1, wherein the damaged skin to which said composition is applied is subject to a wound, scar tissue, decubitus sores, varices, or chronic venous insufficiency conditions.

3. The method of claim 1, wherein said active compound is selected from the group consisting of khellin, visnadine, vincamine, raubasine, tetrahydroalstonine, nicergoline, buflomedil, eburnamonine, and pharmaceutically acceptable derivatives thereof.

4. The method of claim 1, wherein said active compound is selected from the group consisting of visnadine, vincamine, raubasine, nicergoline, buflomedil, a bioflavonoid obtained from Gingko biloba and Cratageus sp. and khellin.

5. The method of claim 4, wherein said composition comprises from about 0.5 to about 1 percent by weight of said compound.

6. The method of claim 1, wherein said composition is a topical medicament which contains from about 0.01 to 10 percent by weight of said active compound.

7. The method of claim 6, wherein said topical medicament is formulated as a salve, ointment, cream, lotion, solution, suspension, stick, spray, plaster, or medicated bandage.

8. The method of claim 1 wherein said composition is in the form of a solution or suspension which further comprises a phospholipid or a silicone.

9. The method of claim 1 wherein the active compound is a coumarin compound which is present in an amount of about 0.01 to 10 percent by weight of the composition.

10. The method of claim 9 wherein the coumarin compound is khellin or visnadine.

11. The method of claim 1 wherein the active compound is a *Vinca alkaloid*, an *Ergot alkaloid* or buflomedil and is present in an amount of about 0.01 to 10 percent by weight of the composition.

12. The method of claim 11 wherein the active compound is vincamine or raubasine.

13. The method of claim 1 wherein the increased number of capillaries which are formed in the new tissue are arranged parallel to the skin surface both as continuous rows along the length of the damaged skin and as discontinuous networks contra-lateral to the length of the damaged skin to promote uniform healing of the damaged skin while avoiding the formation of unaesthetic keloids.

14. A method of treating bedsores in a patient which comprises applying to an area of damaged skin of said patient having bedsores, a pharmaceutical composition comprising a solution or suspension of a silicone; an active compound selected from the group consisting of khellin, Ginkgo biloba dimeric flavons, visnadine, and vincamine; and a pharmaceutically acceptable carrier, said composition applied in an amount effective to increase the number of capillaries in new tissue which forms during healing of the damaged skin to promote healing.

15. The method of claim 14 wherein the silicone is silicone oil or dimethicone and the active compound is khellin or visnadine which is present in an amount of from about 0.01 to about 10 percent by weight of the composition.

16. The method of claim 14 wherein the increased number of capillaries which are formed in the new tissue are arranged parallel to the skin surface both as continuous rows along the length of the damaged skin and as discontinuous networks contra-lateral to the length of the damaged skin to promote uniform healing of the damaged skin while avoiding the formation of unaesthetic keloids.

17. A method for increasing the number of capillaries in damaged skin during healing thereof which comprises applying to the damaged skin a composition comprising a pharmaceutically acceptable carrier and an active compound of an *Amni visnaga* compound or a Ginkgo bioflavinoid, wherein the active compound is applied in an amount sufficient to form an increased number of capillaries in new tissue which forms during healing of the damaged skin.

18. The method of claim 17 wherein the *Amni visnaga* compound is a coumarin compound and is present in an amount of about 0.01 to 10 percent by weight of the composition.

19. The method of claim 18 wherein the coumarin compound is khellin or visnadine.

20. The method of claim 18, wherein said composition is in the form of a solution or suspension which further comprises a phospholipid or a silicone.

21. The method of claim 17 wherein the increased number of capillaries which are formed in the new tissue are arranged parallel to the skin surface both as continuous rows along the length of the damaged skin and as discontinuous networks contra-lateral to the length of the damaged skin to promote uniform healing of the damaged skin while avoiding the formation of unaesthetic keloids.

22. The method of claim 17 wherein the Ginkgo bioflavinoid is a Ginkgo biloba dimeric flavon compound and is present in an amount of about 0.01 to 10 percent by weight of the composition.

23. The method of claim 22, wherein said composition is in the form of a solution or suspension which further comprises a phospholipid or a silicone.

* * * * *